United States Patent [19]

Ooms et al.

[11] Patent Number: 4,868,198
[45] Date of Patent: Sep. 19, 1989

[54] 3-HALOGENOALKYL-1-ARYL-PYRAZOLE PESTICIDES, COMPOSITIONS AND USE

[75] Inventors: Pieter Ooms, Krefeld; Alexander Klausener, Stolberg-Breinig; Bernd Baasner, Leverkusen; Benedikt Becker, Mettmann; Wolfgang Behrenz, Overath; Bernhard Homeyer, Leverkusen, all of Fed. Rep. of Germany

[73] Assignee: Bayer Aktiengesellschaft, Leverkusen, Fed. Rep. of Germany

[21] Appl. No.: 177,561

[22] Filed: Apr. 4, 1988

[30] Foreign Application Priority Data

Apr. 10, 1987 [DE] Fed. Rep. of Germany ....... 3712204

[51] Int. Cl.$^4$ .................... A01N 43/56; C07D 231/14
[52] U.S. Cl. ....................................... 514/406; 548/378
[58] Field of Search .......................... 548/378; 514/406

[56] References Cited

U.S. PATENT DOCUMENTS

| 4,563,210 | 1/1986 | Beck et al. | 548/378 |
| 4,620,865 | 11/1986 | Beck et al. | 548/378 |

FOREIGN PATENT DOCUMENTS

| 0001019 | 3/1979 | European Pat. Off. | 564/251 |
| 0091022 | 10/1983 | European Pat. Off. | 548/247 |
| 0187285 | 7/1986 | European Pat. Off. | 564/310 |
| 3212137 | 10/1983 | Fed. Rep. of Germany | 548/247 |

OTHER PUBLICATIONS

Tanaka et al., "Cycloadditions of N-Rayl-C(Trifluoromethyl)nitrilimines...," J. Heterocyclic Chem. 22, (1985), pp. 565-568.
Tewari et al., "Studies on Nitrile Imines...," Ind. J. Chem., Sect. B, 19B, pp. 217-218 (1980).
Tanaka et al., "Behavior of Trifluoroacetohydrazonoyl Bromide...,", Bull. Chem. Soc. Jpn, 58, pp. 1841-1842 (1985).
J. Am. Chem. Soc., 76, p. 300 (1954).
Ch. Kashima, "Synthetic Reactions Using Isoxazole Compounds," Heterocycles, 12, pp. 1343-1369, (1979).
Comprehensive Org. Chem. 4 (1979), p. 993.
Elnagdi et al., "The Chemistry of 3-Oxoalkanenitriles," Synthesis, pp. 1-26, (1984).
E. Müller, "Methoden zur Herstellung und Unwandling von Diaziridinen," Article (1966).
Hauser and Hudson, "The Acetoacetic Ester Condension and Certain Related Reactions," Organic Reactions, Chapter 9, pp. 267-303.

Primary Examiner—Robert W. Ramsuer
Attorney, Agent, or Firm—Sprung Horn Kramer & Woods

[57] ABSTRACT

Arthropodically active 3-halogenoalkyl-1-arylpyrzoles of the formula

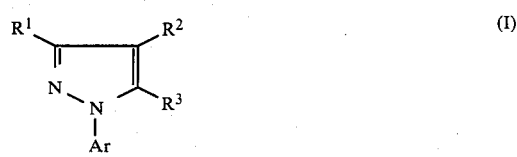

in which
$R^1$ represents halogenoalkyl,
$R^2$ represents cyano, or represents hydroxycarbonyl, or represents carbamoyl or thiocarbamoyl, or represents alkoxycarbonyl, N-alkylcarbamoyl or N,N-dialkylcarbamoyl, or represents alkenyloxycarbonyl, N-alkenylcarbamoyl or N,N-dialkenylcarbamoyl, or represents alkinyloxycarbonyl, N-alkinylcarbamoyl, N,N-dialkinylcarbamoyl or N-arylcarbamoyl, or represents alkylcarbonyl, halogenoalkycarbonyl or cycloalkylcarbonyl,
$R^3$ represents hydrogen, alkyl, halogenoalkyl or cycloalkyl and
Ar represents substituted phenyl, with the exception of the 2,4-dinitrophenyl radical.

7 Claims, No Drawings

3-HALOGENOALKYL-1-ARYL-PYRAZOLE PESTICIDES, COMPOSITIONS AND USE

The invention relates to new 3-halogenoalkyl-1-aryl-pyrazoles, several processes for their preparation and their use as agents for combating pests.

It is already known that certain 5-amino-1-aryl-pyrazoles, such as, for example, 4-cyano-5-propionamido-1-(2,4,6-trichlorophenyl)-pyrazole, have a herbicidal action (compare, for example, DE-OS (German Published Specification) 3,226,513).

Certain 3-halogenoalkyl-1-aryl-pyrazoles, such as, for example, 4-methoxycarbonyl-1-phenyl-3-trifluoromethyl-pyrazole, 4-acetyl-5-methyl-1-(2,4-dinitrophenyl)-3-trichloromethyl-pyrazole, 4-acetyl-5-methyl-1-phenyl-3-trifluoromethyl-pyrazole and 4-methoxycarbonyl-5-methyl-1-phenyl-3-trifluoromethyl-pyrazole, are furthermore known (compare, for example, Bull. chem. Soc. Japan. 59, 2631, [1986]; Chemistry Letters 1982, 543–546; J. Heterocyl. Chem. 22, 565–568 [1985; and Ind. J. Chem., Sect. B, 19B, 217–218 [1980).

Nothing is known of an activity of these already known compounds against pests.

New 3-halogenoalkyl-1-aryl-pyrazoles of the general formula (I)

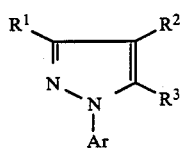

in which
$R^1$ represents halogenoalkyl,
$R^2$ represents cyano, or represents hydroxycarbonyl, or represents carbamoyl or thiocarbamoyl, or represents alkoxycarbonyl, N-alkylcarbamoyl or N,N-dialkylcarbamoyl, or represents alkenyloxycarbonyl, N-alkenylcarbamoyl or N,N-di-alkenylcarbamoyl, or represents alkinyloxycarbonyl, N-alkinylcarbamoyl, N,N-dialkinylcarbamoyl or N-arylcarbamoyl, or represents alkylcarbonyl, halogenoalkylcarbonyl or cycloalkylcarbonyl,
$R^3$ represents hydrogen, alkyl, halogenoalkyl or cycloalkyl and
Ar represents substituted phenyl, with the exception of the 2,4-dinitrophenyl radical,
have been found.

It has furthermore been found that the new 3-halogenoalkyl-1-aryl-pyrazoles of the general formula (I)

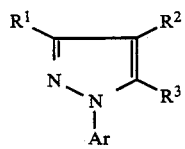

in which
$R^1$ represents halogenoalkyl,
$R^2$ represents cyano, or represents hydroxycarbonyl, or represents carbamoyl or thiocarbamoyl, or represents alkoxycarbonyl, N-alkylcarbamoyl or N,N-dialkylcarbamoyl, or represents alkenyloxycarbonyl, N-alkenylcarbamoyl or N,N-di-alkenylcarbamoyl, or represents alkinyloxycarbonyl, N-alkinylcarbamoyl, N,N-dialkinylcarbamoyl or N-arylcarbamoyl, or represents alkylcarbonyl, halogenoalkylcarbonyl or cycloalkylcarbonyl,
$R^3$ represents hydrogen, alkyl, halogenoalkyl or cycloalkyl and
Ar represents substituted phenyl, with the exception of the 2,4-dinitrophenyl radical,
are obtained by the processes described below.

(a) 3-Halogenoalkyl-1-aryl-pyrazoles of the formula (Ia)

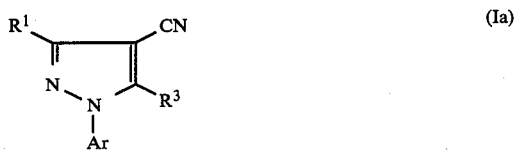

in which $R^1$, $R^3$ and Ar have the abovementioned meaning, are obtained by a process in which N-aryl-hydrazide halides of the formula (II)

in which
Hal represents halogen and
$R^1$ and Ar have the abovementioned meaning,
are reacted with isoxazoles of the formula (III)

in which $R^3$ has the abovementioned meaning, if appropriate in the presence of a diluent and if appropriate in the presence of an acid-binding agent;

(b) 3-halogenoalkyl-1-aryl-pyrazoles of the formula (Ib)

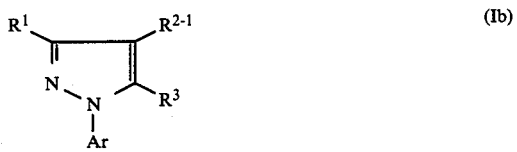

in which
$R^{2-1}$ represents cyano, or represents carbamoyl or thiocarbamoyl, or represents alkoxycarbonyl, N-alkylcarbamoyl or N,N-dialkylcarbamoyl, or represents alkenyloxycarbonyl, N-alkenylcarbamoyl or N,N-dialkenylcarbamoyl, or represents alkinyloxycarbonyl, N-alkinylcarbamoyl, N,N-dialkinylcarbamoyl or N-arylcarbamoyl, or represents alkylcarbonyl, halogenoalkylcarbonyl or cycloalkylcarbonyl and
$R^1$, $R^3$ and Ar have the abovementioned meaning, are obtained by a process in which N-aryl-hydrazide halides of the formula (II)

in which

Hal represents halogen and
R¹ and Ar have the abovementioned meaning,
are reacted either (α) with carbonyl compounds of the formula (IV)

in which R²⁻¹ and R³ have th abovementioned meaning, or (β) with acrylonitrile derivatives of the formula (V)

in which R²⁻¹ and R³ have the abovementioned meanings, or (γ) with alkines of the formula (VI)

in which R²⁻¹ and R³ have the abovementioned meaning, in each case if appropriate in the presence of a diluent and if appropriate in the presence of an acid-binding agent;

(c) 3-halogenoalkyl-1-aryl-pyrazoles of the formula (Ic)

in which
R¹, R³ and Ar have the abovementioned meaning and R²⁻² represents hydroxycarbonyl or carbamoyl, are obtained by a process in which the 3-halogenoalkyl-1-aryl-pyrazoles obtainable with the aid of processes (a) or (b), of the formula (Id)

in which
R¹, R³ and Ar have the abovementioned meaning and R²⁻³ represents cyano, alkoxycarbonyl, alkenyloxycarbonyl or alkinyloxy,
are hydrolyzed at the substituent in the 4-position of the pyrazole ring with acids, if appropriate in the presence of a diluent.

Finally, it has been found that the new 3-halogenoalkyl-1-aryl-pyrazoles of the formula (I) have an insecticidal action.

Surprisingly, the 3-halogenoalkyl-1-aryl-pyrazoles of the general formula (I) according to the invention have a better insecticidal activity than the 5-amino-1-aryl-pyrazoles known from the prior art, such as, for example, 4-cyano-5-propionamido-1-(2,4,6-trichlorophenyl)-pyrazole, which are closely related compounds from the chemical point of view.

Formula (I) provides a general definition of the 3-halogenoalkyl-1-aryl-pyrazoles according to the invention. Preferred compounds of the formula (I) are those in which
R¹ represents straight-chain or branched halogenoalkyl with 1 to 4 carbon atoms and 1 to 9 identical or different halogen atoms,
R² represents cyano, or represents hydroxycarbonyl, or represents carbamoyl or thiocarbamoyl, or represents in each case straight-chain or branched alkoxycarbonyl, N-alkylcarbamoyl or N,N-dialkylcarbamoyl with in each case 1 to 4 carbon atoms in the individual alkyl parts, or represents in each case straight-chain or branched alkenyloxycarbonyl, N-alkenylcarbamoyl or N,N-dialkenylcarbamoyl with in each case 3 to 6 carbon atoms in the individual alkenyl parts, or represents in each case straight-chain or branched alkinyloxycarbonyl, N-alkinylcarbamoyl or N,N-dialkinylcarbamoyl with in each case 3 to 6 carbon atoms in the individual alkinyl parts, or represents phenylcarbamoyl which is optionally substituted in the phenyl part by one or more identical or different substituents, possible substituents being: halogen, cyano, nitro and in each case straight-chain or branched alkyl, alkoxy, alkylthio, halogenoalkyl, halogenoalkoxy or halogenoalkylthio with in each case 1 to 4 carbon atoms and, in the case of the halogenoalkyl, halogenoalkoxy or halogenoalkylthio, with 1 to 9 identical or different halogen atoms; or furthermore represents in each case straight-chain or branched alkylcarbonyl or halogenoalkylcarbonyl with in each case 1 to 5 carbon atoms and, in the case of the halogenoalkylcarbonyl, with 1 to 9 identical or different halogen atoms, or represents cycloalkylcarbonyl with 4 to 8 carbon atoms,
R³ represents hydrogen, or represents in each case straight-chain or branched alkyl or halogenoalkyl with in each case 1 to 4 carbon atoms and, in the case of the halogenoalkyl, with 1 to 9 identical or different halogen atoms, or represents cycloalkyl with 3 to 7 carbon atoms and
Ar represents phenyl which is substituted by one or more identical or different substituents, with the exception of the 2,4-dinitrophenyl radical, possible substituents being: halogen, cyano, nitro and in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl or alkoxycarbonyl with in each case 1 to 4 carbon atoms in the individual alkyl parts and, where appropriate, 1 to 9 identical or different halogen atoms.

Particularly preferred compounds of the formula (I) are those
in which
R¹ represents trifluoromethyl, dichlorofluoromethyl, difluorochloromethyl, difluoromethyl, trifluoroethyl, trifluorochloroethyl, trifluorodichloroethyl, difluorodichloroethyl, tetrafluoroethyl, pentafluoroethyl, heptafluoropropyl or nonafluorobutyl,
R² represents cyano, or represents hydroxycarbonyl, or represents carbamoyl or thiocarbamoyl, or represents methoxycarbonyl, ethoxycarbonyl, N-methylcarbamoyl, N,N-dimethylcarbamoyl, N-ethylcarbamoyl or N,N-diethylcarbamoyl, or represents acetyl, propionyl, trifluoroacetyl, dichlorofluoroacetyl or difluorochloroacetyl, or represents cyclopropylcarbonyl or cyclohexylcarbonyl, or represents N-phenylcarbamoyl which is optionally substituted in the phenyl part by one to three identical or different substituents from the group comprising fluorine, chlorine, bromine, cyano, nitro, methyl, ethyl, n- or i-propyl, methoxy, ethoxy, n- or i-propoxy, methylthio, trifluoromethyl, trifluoromethoxy and trifluoromethylthio, $R^3$ represents hydrogen, methyl, ethyl, n- or i-propyl, n-, i-, s- or t-butyl, trifluoromethyl, dichlorofluoromethyl, difluorochloromethyl, difluoromethyl, trifluoroethyl, tetrafluoroethyl, pentafluoroethyl, trifluorochloroethyl, trifluorodichloroethyl, difluorodichloroethyl, heptafluoropropyl or nonafluorobutyl, or represents cyclopropyl, cyclobutyl, cyclopentyl or cyclohexyl and Ar represents phenyl which is substituted by one to five identical or different substituents, with the exception of the 2,4-dinitrophenyl radical, possible substituents being: fluorine, chlorine, bromine, iodine, cyano, nitro, methyl, ethyl, n-or i-propyl, n-, i-, s- or t-butyl, methoxy, ethoxy, methylthio, methylsulphinyl, methylsulphonyl, methoxycarbonyl, ethoxycarbonyl, trifluoromethyl, dichlorofluoromethyl, difluorochloromethyl, difluoromethyl, pentafluoroethyl, tetrafluoroethyl, trifluorochloroethyl, trifluoroethyl, difluorochloroethyl, trifluorodichloroethyl or a radical $-X-R^4$, X represents oxygen, sulphur, sulphinyl or sulphonyl and $R^4$ represents trifluoromethyl, dichlorofluoromethyl, difluorochloromethyl, difluoromethyl, pentafluoroethyl, tetrafluoroethyl, trifluorochloroethyl, trifluoroethyl, difluorochloroethyl or trifluorodichloroethyl.

The following 3-halogenoalkyl-1-aryl-pyrazoles of the general formula (I) may be mentioned specifically, in addition to the compounds mentioned in the preparation examples:

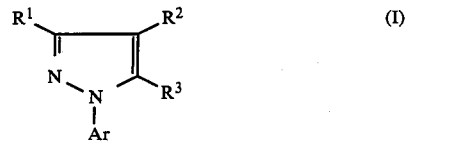

| $R^1$ | $R^2$ | $R^3$ | Ar |
|---|---|---|---|
| $CF_3$ | $CONH_2$ | $CH_3$ | 2,6-Cl, 4-$SO_2CF_3$ phenyl |
| $CF_3$ | $CSNH_2$ | $CH_3$ | 2,6-Cl, 4-$SO_2CF_3$ phenyl |
| $CF_3$ | $COOC_2H_5$ | $CH_3$ | 2,6-Cl, 4-$SO_2CF_3$ phenyl |
| $CF_3$ | $COOH$ | $CH_3$ | 2,6-Cl, 4-$SO_2CF_3$ phenyl |
| $CF_3$ | $CONH_2$ | $CH_3$ | 2-Cl, 4-$CF_3$ phenyl |
| $CF_3$ | $CSNH_2$ | $CH_3$ | 2-Cl, 4-$CF_3$ phenyl |
| $CF_3$ | $COOC_2H_5$ | $CH_3$ | 2-Cl, 4-$CF_3$ phenyl |
| $CF_3$ | $COOH$ | $CH_3$ | 2-Cl, 4-$CF_3$ phenyl |
| $CF_3$ | $CONH_2$ | $CH_3$ | 2-Cl, 4-$CF_3$, 5-F phenyl |
| $CF_3$ | $CONH_2$ | $H$ | 2-Cl, 4-$CF_3$, 5-F phenyl |
| $CF_3$ | $CSNH_2$ | $CH_3$ | 2-Cl, 4-$CF_3$, 5-F phenyl |

-continued $$\underset{Ar}{\underset{|}{N-N}}\overset{R^1}{\underset{R^3}{\bigvee}}\overset{R^2}{\phantom{R^3}} \quad (I)$$

| R[1] | R[2] | R[3] | Ar |
|---|---|---|---|
| CF$_3$ | CSNH$_2$ | H | 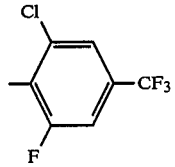 |
| CF$_3$ | CONH$_2$ | CH$_3$ | 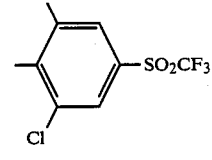 |
| CF$_3$ | CONH$_2$ | H | 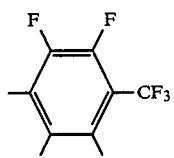 |
| CF$_3$ | CN | H | 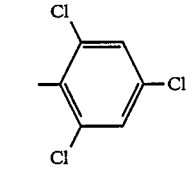 |
| CF$_3$ | CN | CH$_3$ | 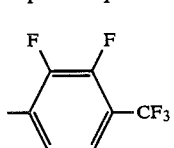 |
| CF$_3$ | CN | CF$_3$ | 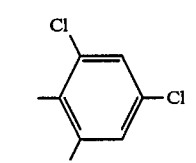 |
| CF$_3$ | CSNH$_2$ | CH$_3$ | 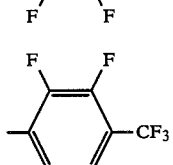 |
| CF$_3$ | CSNH$_2$ | H | 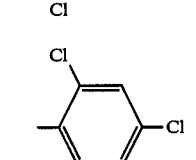 |

-continued $$\underset{Ar}{\underset{|}{N-N}}\overset{R^1}{\underset{R^3}{\bigvee}}\overset{R^2}{\phantom{R^3}} \quad (I)$$

| R[1] | R[2] | R[3] | Ar |
|---|---|---|---|
| CF$_3$ | COOC$_2$H$_5$ | H | 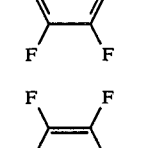 |
| CF$_3$ | COOH | CH$_3$ | 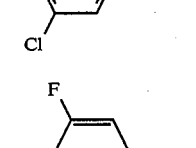 |
| CF$_3$ | COOC$_2$H$_5$ | CH$_3$ | 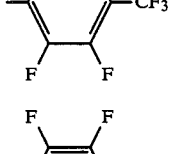 |
| CF$_3$ | CONH$_2$ | CH$_3$ | 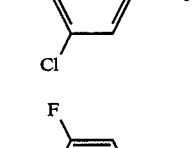 |
| CF$_3$ | COOH | H | 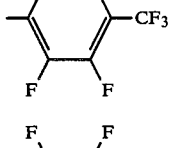 |
| CF$_3$ | COOH | CH$_3$ | 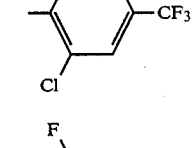 |
| CF$_3$ | COOC$_2$H$_5$ | CH$_3$ | 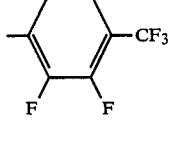 |
| CF$_3$ | CN | CH$_3$ | 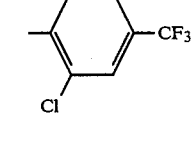 |

-continued
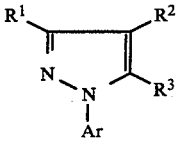  (I)
| R¹ | R² | R³ | Ar |
|---|---|---|---|
| $CF_3$ | CN | H | 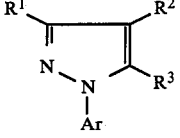 |
| $CF_3$ | CN | $CF_3$ | 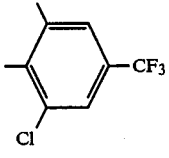 |
| $CF_3$ | COOH | H | 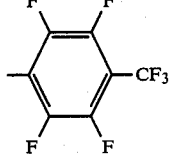 |
| $CF_3$ | $COOC_2H_5$ | H | 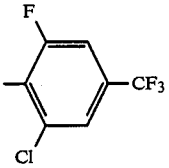 |
| $CF_3$ | COOH | $CF_3$ | 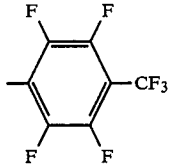 |
| $CF_3$ | $COOC_2H_5$ | $CF_3$ | 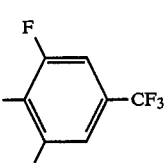 |
| $CF_3$ | $COOC_2H_5$ | $CH_3$ | 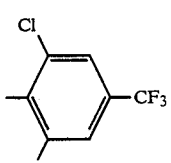 |
| $CF_3$ | COOH | $CH_3$ | 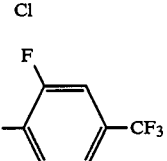 |
-continued
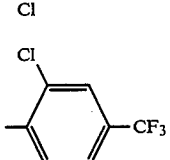  (I)
| R¹ | R² | R³ | Ar |
|---|---|---|---|
| $CF_3$ | $COOC_2H_5$ | H | 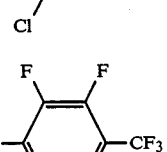 |
| $CF_3$ | COOH | H | 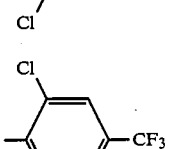 |
| $C_2F_5$ | CN | $CH_3$ | 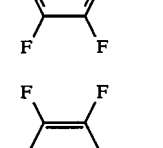 |
| $C_2F_5$ | CN | H | 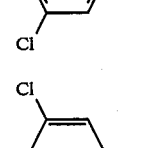 |
| $C_2F_5$ | CN | $CF_3$ | 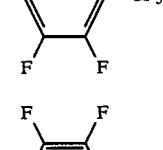 |
| $C_2F_5$ | $CONH_2$ | $CH_3$ | 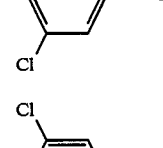 |
| $C_2F_5$ | $CONH_2$ | H | 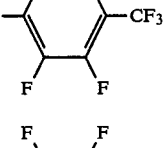 |
| $C_2F_5$ | $CSNH_2$ | $CH_3$ | 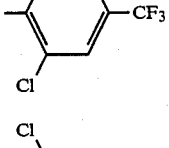 |

-continued $$\begin{array}{c} R^1 \diagdown \diagup R^2 \\ N \diagdown N \diagup R^3 \\ | \\ Ar \end{array} \quad (I)$$

| R¹ | R² | R³ | Ar |
|---|---|---|---|
| C₂F₅ | CSNH₂ | H | 2,6-Cl₂-4-CF₃-C₆H₂ |
| C₂F₅ | COOC₂H₅ | H | 2,6-Cl₂-4-CF₃-C₆H₂ |
| C₂F₅ | COOC₂H₅ | CH₃ | 2,6-Cl₂-4-CF₃-C₆H₂ |
| C₂F₅ | COOC₂H₅ | CF₃ | 2,6-Cl₂-4-CF₃-C₆H₂ |
| C₂F₅ | COOH | C₂F₅ | 2,6-Cl₂-4-CF₃-C₆H₂ |
| C₃F₇ | CN | C₃F₇ | 2,6-Cl₂-4-CF₃-C₆H₂ |
| C₃F₇ | CN | CH₃ | 2,6-Cl₂-4-CF₃-C₆H₂ |
| C₃F₇ | CN | H | 2,6-Cl₂-4-CF₃-C₆H₂ |
| C₃F₇ | CONH₂ | CH₃ | 2,6-Cl₂-4-CF₃-C₆H₂ |
| C₃F₇ | CSNH₂ | H | 2,6-Cl₂-4-CF₃-C₆H₂ |
| C₃F₇ | COOC₂H₅ | CH₃ | 2,6-Cl₂-4-CF₃-C₆H₂ |
| C₃F₇ | COOH | CH₃ | 2,6-Cl₂-4-CF₃-C₆H₂ |
| CCl₂F | CN | CH₃ | 2,6-Cl₂-4-CF₃-C₆H₂ |
| CCl₂F | CONH₂ | H | 2,6-Cl₂-4-CF₃-C₆H₂ |
| CCl₂F | CSNH₂ | CH₃ | 2,6-Cl₂-4-CF₃-C₆H₂ |
| CCl₂F | COOC₂H₅ | CCl₂F | 2,6-Cl₂-4-CF₃-C₆H₂ |

-continued $$\underset{\underset{Ar}{|}}{\overset{R^1}{\underset{N}{\bigwedge}}\overset{R^2}{\underset{N}{\bigvee}}R^3} \quad (I)$$

| R¹ | R² | R³ | Ar |
|---|---|---|---|
| CCl₂F | COOH | H | 2,6-dichloro-4-(trifluoromethyl)phenyl |
| CF₃ | CONHCH₃ | CF₃ | 2,6-dichloro-4-(trifluoromethyl)phenyl |
| CF₃ | CONH₂ | H | 2,6-dichloro-4-(trifluoromethylsulfonyl)phenyl |
| CF₃ | CSNH₂ | H | 2,6-dichloro-4-(trifluoromethylsulfonyl)phenyl |
| CF₃ | CONH₂ | H | 2-chloro-4-(trifluoromethyl)phenyl |
| CF₃ | COOC₂H₅ | H | 2-chloro-4-(trifluoromethyl)phenyl |
| CF₃ | COOH | H | 2-chloro-4-(trifluoromethyl)phenyl |
| CF₃ | CSNH₂ | H | 2-chloro-4-(trifluoromethyl)phenyl |
| CF₃ | CN | H | 2-chloro-4-(trifluoromethyl)phenyl |
| CF₃ | CN | CH₃ | 2-chloro-4-(trifluoromethyl)phenyl |
| CF₃ | CN | CF₃ | 2-chloro-4-(trifluoromethyl)phenyl |
| C₂F₅ | CN | H | 2-fluoro-6-chloro-4-(trifluoromethyl)phenyl |
| C₂F₅ | CN | CH₃ | 2-fluoro-6-chloro-4-(trifluoromethyl)phenyl |
| C₂F₅ | CN | CF₃ | 2-fluoro-6-chloro-4-(trifluoromethyl)phenyl |
| C₂F₅ | CONH₂ | CH₃ | 2-fluoro-6-chloro-4-(trifluoromethyl)phenyl |
| C₂F₅ | COOC₂H₅ | CH₃ | 2-fluoro-6-chloro-4-(trifluoromethyl)phenyl |
| C₂F₅ | COOH | CH₃ | 2-fluoro-6-chloro-4-(trifluoromethyl)phenyl |

-continued

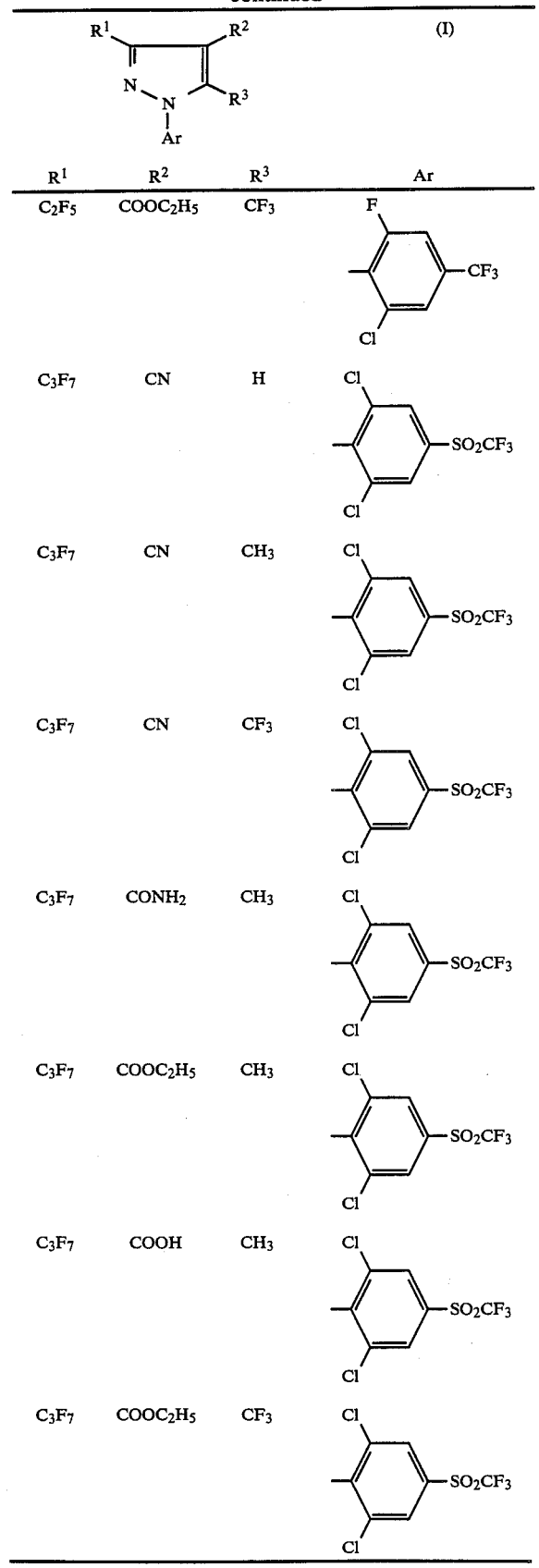

| R¹ | R² | R³ | Ar |
|---|---|---|---|
| C₂F₅ | COOC₂H₅ | CF₃ | ![4-CF₃-2-F-6-Cl-phenyl] |
| C₃F₇ | CN | H | ![2,6-Cl₂-4-SO₂CF₃-phenyl] |
| C₃F₇ | CN | CH₃ | ![2,6-Cl₂-4-SO₂CF₃-phenyl] |
| C₃F₇ | CN | CF₃ | ![2,6-Cl₂-4-SO₂CF₃-phenyl] |
| C₃F₇ | CONH₂ | CH₃ | ![2,6-Cl₂-4-SO₂CF₃-phenyl] |
| C₃F₇ | COOC₂H₅ | CH₃ | ![2,6-Cl₂-4-SO₂CF₃-phenyl] |
| C₃F₇ | COOH | CH₃ | ![2,6-Cl₂-4-SO₂CF₃-phenyl] |
| C₃F₇ | COOC₂H₅ | CF₃ | ![2,6-Cl₂-4-SO₂CF₃-phenyl] |

If, for example, N-(2-chloro-6-fluoro-4-trifluoromethylphenyl)-trifluoroacetohydrazide bromide and isoxazole are used as starting substances, the course of the reaction in process (a) according to the invention can be represented by the following equation:

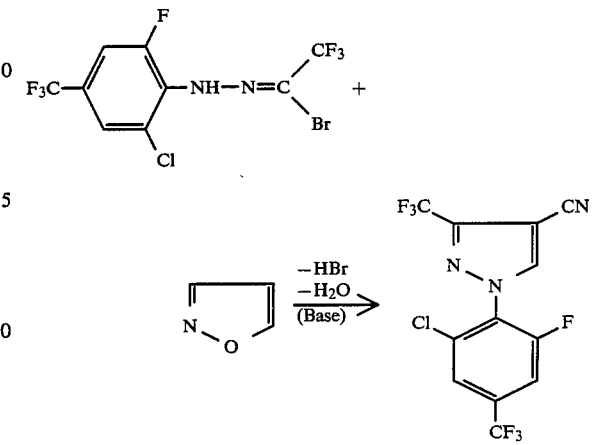

If, for example, N-(2,4,6-trichlorophenyl)-trifluoroacetohydrazide bromide and ethyl acetoacetate are used as starting substances, the course of the reaction in process (b-α) according to the invention can be represented by the following equation:

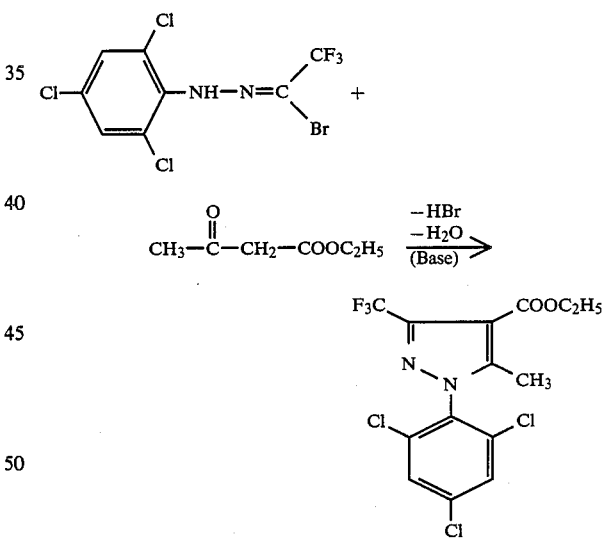

If, for example, N-(2,3,6-trichloro-4-trifluoromethylphenyl)-trifluoroacetohydrazide bromide and fumaric acid dinitrile are used as starting substances, the course of the reaction in process (bβ) according to the invention can be represented by the following equation:

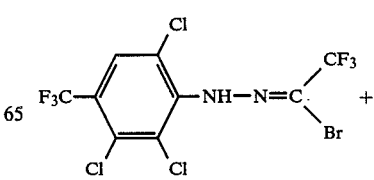

-continued

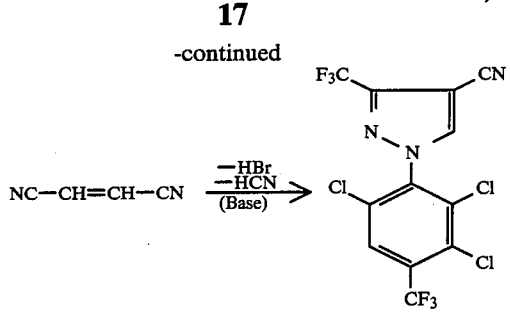

If, for example, N-(2,6-dichloro-4-trifluoromethylphenyl)-trifluoroacetohydrazide bromide and methyl propionate are used as starting substances, the course of the reaction in process (b-γ) according to the invention can be represented by the following equation:

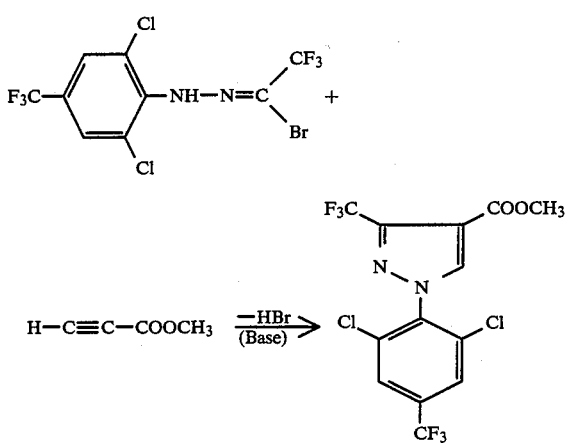

If, for example, 4-ethoxycarbonyl-3,5-bis-(trifluoromethyl)-1-(2,3,5,6-tetrafluoro-4-trifluoromethylphenyl)-pyrazole and sulphuric acid are used as starting compounds, the course of the reaction in process (c) according to the invention can be represented by the following equation:

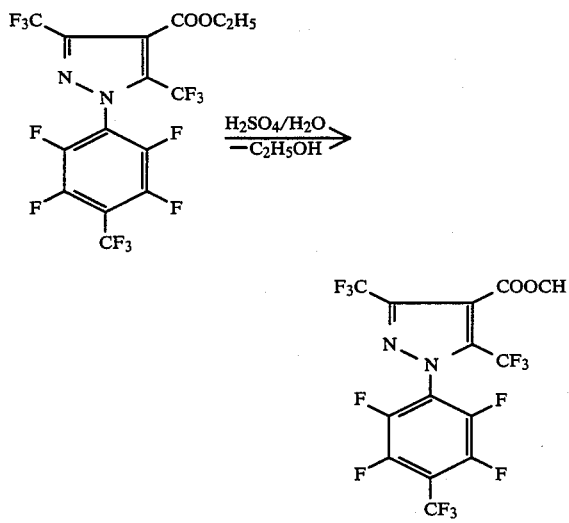

Formula (II) provides a general definition of the N-arylhydrazide halides required as starting substances for carrying out processes (a) and (b) according to the invention. In this formula (II), $R^1$ and Ar preferably represent those radicals which have already been mentioned as preferred for these substituents in connection with the description of the substances of the formula (I) according to the invention. Hal preferably represents chlorine or bromine.

The N-arylhydrazide halides of the formula (II) are known in some cases (compare, for example, Chem. Lett. 1982, 543; J. Heterocycl. Chem. 22, 565 [1985]; and European Pat. No. 1,019).

They are obtained, for example, by a process in which arylhydrazines of the formula (VII)

in which Ar has the abovementioned meaning, are initially reacted with aldehydes of the formula (VIII)

in which $R^1$ has the abovementioned meaning, or with their hydrates or hemi-acetals of the formula (IX)

in which
$R^1$ has the abovementioned meaning and
$R^5$ represents hydrogen or alkyl, in a first stage, if appropriate in the presence of a diluent, such as, for example, ethanol or toluene, and if appropriate in the presence of a reaction auxiliary, such as, for example, sulphuric acid, at temperatures between $-30°$ C. and $+150°$ C., and the arylhydrazones thus obtainable, of the formula (X)

in which $R^1$ and Ar have the abovementioned meaning, are reacted in a 2nd stage with halogenating agents, such as, for example, N-bromosuccinimide, N-chlorosuccinimide or bromine, if appropriate in the presence of a diluent, such as, for example, dimethylformamide or acetic acid, at temperatures between $-30°$ C. and $=100°$ C.

The N-arylhydrazones of the formula (X) are known in some cases (compare, for example, Bull. Chem. Soc. Japan 58, 1841 (1985); J. Heterocyclic Chem. 22, 565 (1985); and Chem. Lett. 1982, 543).

The aldehydes of the formula (VIII) and their hydrates or hemi-acetals of the formula (IX) are generally known compounds of organic chemistry (compare, for example, J. Am. chem. Soc., 76, 300 [1954]).

The arylhydrazines of the formula (VII) are known (compare, for example, European Pat. No. 154,115, European Pat. No. 187,285 and European Pat. No. 34,945), or they are obtainable analogously to known compounds by generally known processes (compare, for example, Houben-Weyl, "'Methoden der organischen Chemie" ("Methods of Organic Chemistry"), Volume X, 2, Thieme Verlag, Stuttgart 1967).

Formula (III) provides a general definition of the isoxazoles furthermore required as starting substances for carrying out process (a) according to the invention.

In this formula (III), $R^3$ preferably represents those radicals which have already been mentioned as preferred for this substituent in connection with the description of the substances of the formula (I) according to the invention.

The isoxazoles of the formula (III) are in most cases generally known compounds of organic chemistry (compare, for example, DE-OS (German Published Specification) 3,212,137, European Pat. No. 91,022, Heterocycles 12, 1343 [1979]; Comprehensive Org. Chemistry 4, 993 [1979]).

Isoxazoles of the formula (IIIa)

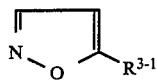 (IIIa)

in which $R^{3-1}$ represents fluoroalkyl, in particular trifluoromethyl, dichlorofluoromethyl or chlorodifluoromethyl, are the subject matter of German patent application P 36 42 453 of December 12, 1986, corresponding to U.S. application S.N. 125296 filed 11/23/87.

They are obtained, for example, by a process in which isoxazoles of the formula (IIIb)

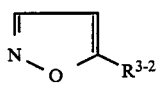 (IIIb)

in which $R^{3-2}$ represents chloroalkyl, in particular trichloromethyl, are reacted with fluorinating agents, such as, for example, hydrogen fluoride or antimony trifluoride, in the gas phase at temperatures between 50° C. and 250° C. under a pressure of between 1 and 50 bar.

Chloroalkyl-isoxazoles of the formula (IIIb) are known (compare, for example, Synthesis 1986, 69–70).

Formula (IV) provides a general definition of the carbonyl compounds furthermore required as starting substances for carrying out process (b-α) according to the invention. In this formula (IV), $R^3$ preferably represents those radicals which have already been mentioned as preferred for this substituent in connection with the description of the substances of the formula (I) according to the invention. $R^{2-1}$ preferably represents those radicals which have already been mentioned as preferred for the substituent $R^2$ in connection with the description of the substances of the formula (I) according to the invention, with the exception of the hydroxycarbonyl radical.

The carbonyl compounds of the formula (IV) are generally known compounds of organic chemistry (compare, for example, Organic Reactions 1, 266 [1947]; and Synthesis 1984, 1).

Formula (V) provides a general definition of the acrylonitrile derivatives furthermore required as starting substances for carrying out process (b-β) according to the invention. In this formula (V), $R^3$ preferably represents those radicals which have already been mentioned as preferred for this substituent in connection with the description of the substances of the formula (I) according to the invention. $R^{2-1}$ preferably represents those radicals which have already been mentioned as preferred for the substituent $R^2$ in connection with the description of the substances of the formula (I) according to the invention, with the exception of the hydroxycarbonyl radical.

The acrylonitrile derivatives of the formula (V) are generally known compounds of organic chemistry.

Formula (VI) provides a general definition of the alkines furthermore required as starting substances for carrying out process (b-γ) according to the invention. In this formula (VI), $R^3$ preferably represents those radicals which have already been mentioned as preferred for this substituent in connection with the description of the substances of the formula (I) according to the invention. $R^{2-1}$ preferably represents those radicals which have already been mentioned as preferred for the substituent $R^2$ in connection with the description of the substances of the formula (I) according to the invention, with the exception of the hydroxycarbonyl radical.

The alkines of the formula (VI) are generally known compounds of organic chemistry (compare, for example, Houben-Weyl "Methoden der organischen Chemie" ("Methods of Organic chemistry"), Volume V/2a, page 1, Thieme Verlag Stuttgart 1977).

The 3-halogenoalkyl-1-aryl-pyrazoles required as starting materials for carrying out process variant (C) according to the invention are defined generally by formula (Id). In this formula (Id) $R^1$, $R^3$ and Ar preferably represent those radicals which have already been mentioned as preferred radicals for these substituents in connection with the description of the compounds of formula (I) according to the invention. $R^{2-3}$ preferably represent cyano or straight-chain or branched alkoxycarbonyl with 1 to 4 carbon atoms, in particular cyano, methoxycarbonyl or ethoxycarbonyl.

The 3-halogenoalkyl-1-aryl-pyrazoles of the formula (Id) are compounds according to the invention and are obtainable with the aid of process variants (a) or (b) according to the invention.

Possible diluents for carrying out the process variants (a) and (b-α) according to the invention are inert organic solvents. Polar solvents such as for example dioxane, tetrahydrofuran, dimethyl formamide, ethanol, methanol, t-butanol or ethylene glycol monomethyl ether are preferably used.

The process variants (a) and (b-α) according to the invention are preferably carried out in the presence of a suitable acid-binding agent. All the commonly usable inorganic or organic bases can be used as acid-binding agents. Alkali metal hydrides, hydroxides or alcoholates, such as for example sodium hydride, sodium hydroxide, sodium methylate, sodium ethylate, sodium isopropylate, potassium isopropylate or potassium t-butylate are preferably used.

The reaction temperatures can be varied over a relatively large range when carrying out process variants (a) and (b-α) according to the invention. In general temperatures between −30° C. and +150° C., preferably temperatures between 0° C. and +100° C. are used.

Formula (Id) provides a general definition of the 2.0 mols, of isoxazoles of the formula (III) and if appropriate 1.0 to 10 mols, preferably 1.0 to 2.0 mols of acid-binding agent are employed per mol of N-arylhydrazide halide of the formula (II). The reaction is carried out and the reaction products of the formula (Ia) are worked up and isolated by generally known processes (compare also the preparation examples).

For carrying out process (b-α)according to the invention, in general 1.0 to 10.0 mols, preferably 1.0 to 2.0 mols of carbonyl compound of the formula (IV) and if appropriate 1.0 to 10.0 mols, preferably 1.0 to 2.0 mols, of acid-binding agent are employed per mol of N-arylhydrazide halide of the formula (II). The reaction is carried out and the reaction products of the formula (Ib) are worked up and isolated by generally known processes (compare also the preparation examples).

Possible diluents for carrying out processes (b-β) and (b-γ) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric acid triamide, or esters, such as ethyl acetate.

Processes (b-β) and (b-γ) according to the invention are preferably carried out in the presence of a suitable acid-binding agent. Possible acid-binding agents are all the customary inorganic or organic bases. Bases which are preferably used are tertiary amines, such as triethylamine, N,N-dimethylaniline, pyridine, diazabicyclooctane (DABCO), diazabicyclononene (DBN) or diazabicyloundecene (DBU).

The reaction temperatures can be varied within a substantial range in carrying out processes (b-β) and (b-γ) according to the invention. The reaction is in general carried out at temperatures between −30° C. and +150° C., preferably at temperatures between 0° C. and 100° C.

For carrying out process (b-β) according to the invention, in general 1.0 to 20.0 mols, preferably 1.0 to 5.0 mols of acrylonitrile derivative of the formula (V) and if appropriate 1.0 to 20.0 mols preferably 1.0 to 2.0 mols, of acid-binding agent are employed per mol of N-arylhydrazide halide of the formula (II).

The reaction is carried out and the reaction products are worked up and isolated by generally customary methods (compare also the preparation examples).

For carrying out process (b-γ) according to the invention, in general 1.0 to 20.0 mols, preferably 1.0 to 5.0 mols, of alkine of the formula (VI) and if appropriate 1.0 to 20.0 mols, preferably 1.0 to 2.0 mols, of acid-binding agent are employed per mol of N-arylhydrazide halide of the formula (II).

The reaction is carried out and the reaction products are worked up and isolated by generally customary methods (compare also the preparation examples).

Process (c) according to the invention is carried out in the presence of a suitable acid. Possible acids are all the inorganic or organic acids which can usually be employed. Sulphuric acid, hydrochloric acid or p-toluenesulphonic acid is preferably used.

Possible diluents for carrying out process (c) according to the invention are polar inorganic or organic solvents or mixtures thereof with water. The sulphuric acid employed as a reagent is preferably simultaneously used as the diluent in an appropriate excess.

The reaction temperatures can be varied within a substantial range in carrying out process (c) according to the invention. The reaction is in general carried out at temperatures between 0° C. and +150° C., preferably at temperatures between +20° C. and +100° C.

For carrying out process (c) according to the invention, in general 1.0 to 30 mols, preferably 1.0 to 10.0 mols, of aqueous acid are employed per mol of 3-halogenoalkyl-1-aryl-pyrazole of the formula (Id). The reaction is carried out and the reaction products are worked up and isolated by generally known processes (compare also the preparation examples).

The active compounds are suitable for combating animal pests, preferably arthropods, and in particular insects, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*. From the order of the Dermaptera, for example, *Forficula auricularia*. From the order of the Isoptera, for example, *Reticulitermes spp*. From the order of the Anoplura, for example, *Phylloxera vastatrix, Pemphigus spp., Pediculus humanus corporis, Haematopinus spp.* and *Linognathus spp*. From the order of the Mallophaga, for example, *Trichodectes spp.* and *Damalinea spp.*

From the order of the Thysanoptera, for example, *Hercinothrips femoralis* and *Thrips tabaci*. From the order of the Heteroptera, for example, *Eurygaster spp., Dysdercus intermedius, Piesma quadrata, Cimex lectularius, Rhodnius prolixus* and *Triatoma spp*. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp*. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Ato-*

*maria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis* and *Costelytra zealandica.*

From the order of the Hymenoptera, for example, *Diprion spp., Hoplocampa spp., Lasius spp., Monomorium pharaonis* and *Vespa spp.* From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphoaptera, for example, *Xenopsylla cheopis* and *Ceratophyllus spp.*

The active compounds according to the invention can thereby be used with particularly good success for combating leaf and soil insects, such as, for example, against the larvae of the horseradish leaf beetle (*Phaedon cochleariae*), or against grubs of the onion fly (*Phorbia antiqua*), and against adult forms of the horseradish leaf beetle (*Phaedon cochleariae*). In this application, the active compounds according to the invention also exhibit outstanding systemic properties, as well as a good protective activity. In addition, the active compounds according to the invention can be employed particularly successfully for combating hygiene pests and pests of stored products, such as, for example, against the common house fly (*Musca domestica*) or against the German cockroach (*Blattella germanica*).

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and into formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carries are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molydenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

PREPARATION EXAMPLES

Example 1

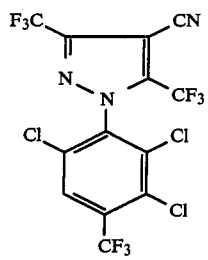

(Process a)

0.92 g (0.04 mol) of sodium is dissolved in 25 ml of ethanol, 5.48 g (0.04 mol) of 5-trifluoromethylisoxazole are added at 0° C. and the mixture is stirred at room temperature for 15 minutes. 16.16 g (0.04 mol) of N-(2,6-dichloro-4-trifluoromethylphenyl)-trifluoroacetohydrazide bromide are added dropwise to this mixture, while cooling, and the mixture is subsequently stirred at 25° C. for a further 10 hours. After the sodium bromide which has precipitated out is filtered off, the filtrate is concentrated and the residue is separatad by column chromatography. 1.65 g (9.3% of theory) of 4-cyano-3,5-di(trifluoromethyl)-1-(2,6-dichloro-4-trifluoromethylphenyl)-pyrazole of melting point 88° C.–92° C. are obtained.

PREPARATION OF THE STARTING COMPOUND

Example III-1

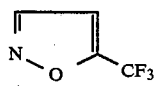

56 g (0.3 mol) of 5-trichloromethyl-isoxazole (compare, for example, DE-OS (German Published Specification) 3,212,137), 80 g of antimony trifluoride and 1 ml of antimony pentachloride are brought together at room temperature and the mixture is then heated up to an internal temperature of 140° C. and allowed to react at this temperature under reflux for 90 minutes. The volatile constituents are then distilled off under normal pressure (70° C. to 120° C.) and the crude product obtained is redistilled over a 10 cm packed column.

26.8 g (65.2% of theory) of 5-trifluoromethyl-isoxazole are obtained with a boiling point of 79° C. to 80° C. under normal pressure and a refractive index $n_D^{20} = 1.3493$.

Example 2

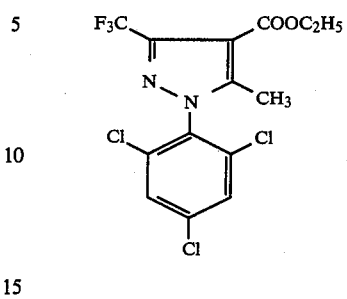

(Process b-α)

5.20 g (0.04 mol) of ethyl acetoacetate are added to a solution of 2.72 g (0.04 mol) of sodium ethanolate in 20 ml of ethanol and the mixture is heated to the reflux temperature for 15 minutes. 14.8 g (0.04 mol) of N-(2,4,6-trichlorophenyl)-trifluoroacetohydrazide bromide are then added dropwise and the mixture is boiled at the reflux temperature for a further 5 hours. After cooling to room temperature, the sodium bromide which has precipitated out is filtered off and the filtrate is concentrated.

Separation of the residue by column chromatography gives 4.56 g (28% of theory) of 4-ethoxycarbonyl-5-methyl-3-trifluoromethyl-1-(2,4,6-trichlorophenyl)-pyrazole of melting point 95° C.–96° C.

Example 3

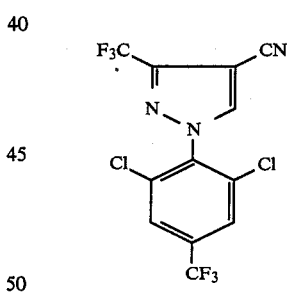

(Process b-β)

12.6 g (0.125 mol) of triethylamine are added dropwise to a mixture of 20.2 g (0.05 mol) of N-(2,6-dichloro-4-trifluoromethylphenyl)-trifluoroacetohydrazide bromide, 7.8 g (0.10 mol) of fumaric acid dinitrile and 20 ml of toluene at 90° C., while stirring. The mixture is stirred at 90° C. for a further 5 hours, cooled and concentrated.

Separation of the residue by column chromatography gives 2.79 g (15% of theory) of 4-cyano-3-trifluoromethyl-1-(2,6-dichloro-4-trifluoromethylphenyl)-pyrazole of melting point 116° C.–118° C.

Example 4

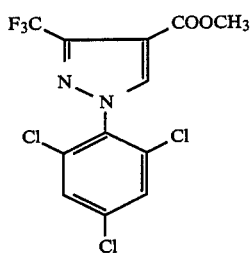

(Process b-γ)

8.86 g (0.088 mol) of triethylamine are added dropwise to a mixture of 12.97 g (0.035 mol) of N-2,4,6-trichlorophenyl)-trifluoroacetohydrazide bromide, 6.47 g (0.077 mol) of methyl propiolate and 25 ml of toluene at 75° C. and the mixture is subsequently stirred at 75° C. for a further 2 hours. After cooling to room temperature, the sodium bromide is filtered off and the filtrate is concentrated.

Column chromatography gives 5.79 g (44.3% of theory) of 4-methoxycarbonyl-3-trifluoromethyl-1-(2,4,6-trichlorophenyl)-pyrazole of melting point 107° C.–108° C.

Example 5

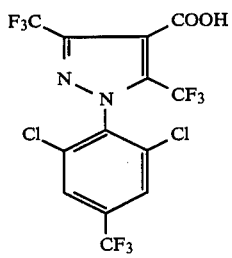

(Process c)

A mixture of 0.98 g (0.002 mol (of 4-ethoxycarbonyl-3,5-di(trifluoromethyl)-1-(2,6-dichloro-4-trifluoromethylphenyl)-pyrazole and 4 ml of concentrated sulphuric acid is heated at 75° C. for 5 hours and then poured onto ice.

Filtration with suction gives 0.79 g (86% of theory) of 4-hydroxycarbonyl-3,5-di(trifluoromethyl)-1-(2,6-dichloro-4-trifluoromethylphenyl)-pyrazole of melting point 185° C.–190° C.

Example 6

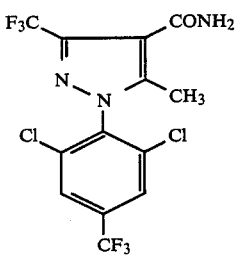

(Process c)

0.97 g (0.0025 mol) of 4-cyano-5-methyl-3-trifluoromethyl-1-(2,6-dichloro-4-trifluoromethylphenyl)-pyrazole in 4 ml of concentrated sulphuric acid are heated at 75° C. for 5 hours. After cooling to room temperature, the mixture is diluted with ice-water and filtered with suction.

0.70 g (69% of theory) of 4-aminocarbonyl-5-methyl-3-trifluoromethyl-1-(2,6-dichloro-4-trifluoromethylphenyl)-pyrazole of melting point 165° C.–170° C. is obtained.

The 3-halogenoalkyl-1-aryl-pyrazoles of the general formula (I) listed in the following table are obtained in a corresponding manner and in accordance with the general statements on the preparation:

| Ex. No. | $R^1$ | $R^2$ | $R^3$ | Ar | Melting point/°C. |
|---|---|---|---|---|---|
| 7 | $CF_3$ | $COOCH_3$ | H | 2,4-dichloro-5-trifluoromethylphenyl | 92–93 |
| 8 | $CF_3$ | $COOC_2H_5$ | $CF_3$ | 2,4,6-trichlorophenyl | 51–55 |

-continued
| | | | | | (I) |
|---|---|---|---|---|---|
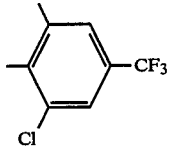
| Ex. No. | R¹ | R² | R³ | Ar | Melting point/°C. |
|---|---|---|---|---|---|
| 9 | $CF_3$ | $COOC_2H_5$ | $CF_3$ | 2,6-Cl, 4-$CF_3$-phenyl | 74–75 |
| 10 | $CF_3$ | $COOC_2H_5$ | $CH_3$ | 2,6-Cl, 4-$CF_3$-phenyl | 91–93 |
| 11 | $CF_3$ | $COOC_2H_5$ | cyclopropyl | 2,6-Cl, 4-$CF_3$-phenyl | 98–110 |
| 12 | $CF_3$ | $CO-CH_3$ | $CF_3$ | 2,6-Cl, 4-$CF_3$-phenyl | 55–57 |
| 13 | $CF_3$ | $CN$ | $CH_3$ | 2,6-Cl, 4-$CF_3$-phenyl | 90–92 |
| 14 | $CF_3$ | $CN$ | H | 2,3,6-Cl, 4-$CF_3$-phenyl | 142–145 |
| 15 | $CF_3$ | $CN$ | H | 2,4,6-Cl-phenyl | 116–117 |
| 16 | $CF_3$ | $CN$ | $CH_3$ | 2,4,6-Cl-phenyl | 140–144 |

-continued $$\underset{\underset{Ar}{|}}{\underset{N}{\overset{R^1}{\underset{\diagdown}{N}}\diagup}\overset{R^2}{\underset{\diagup}{\diagdown}}\overset{}{\underset{}{\diagdown}}R^3} \qquad (I)$$

| Ex. No. | R¹ | R² | R³ | Ar | Melting point/°C |
|---|---|---|---|---|---|
| 17 | CF₃ | CN | CH₃ | 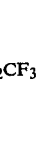 | 149–150 |
| 18 | CF₃ | CN | CCl₂F | 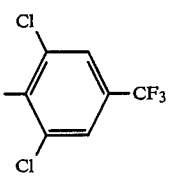 | 95–96 |
| 19 | CF₃ | CN | H | 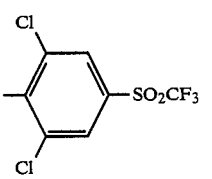 | 131–135 |
| 20 | CF₃ | CN | CClF₂ | 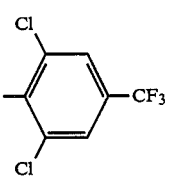 | 80–82 |

PREPARATION OF THE STARTING COMPOUNDS

Example II-1

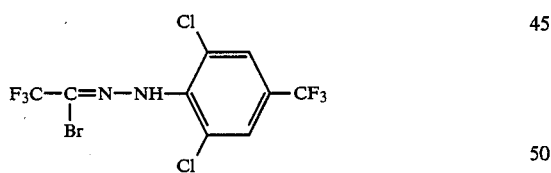

4.45 g (0.025 mol) of N-bromosuccinimide are added in portions to a solution of 8.12 g (0.025 mol) of trifluoroacetaldehyde N-(2,6-dichloro-4-trifluoromethylphenyl)-hydrazone in 7.5 ml of dimethylformamide at room temperature, whereupon an exothermic reaction occurs. The mixture is stirred at room temperature for 3 hours, the dimethylformamide is distilled off and 20 ml of petroleum ether are added to the residue. After the succinimide which has precipitated out has been filtered off with suction, the filtrate is concentrated and the residue is subjected to bulb tube distillation.

9.26 g (91.7% of theory) of N-(2,6-dichloro-4-trifluoromethylphenyl)-trifluoroacetohydrazide bromide of boiling point 110° C. under 0.06 mbar and of refractive index $n_D^{20}$ 1.510 are obtained.

Example II-2

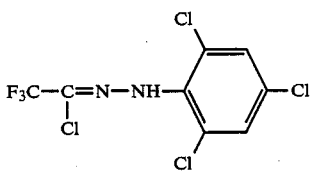

3.2 g (0.011 mol) of trifluoroacetaldehyde N-(2,4,6-trichlorophenyl)-hydrazone and 1.5 g (0.011 mol) of N-chlorosuccinimide in 3.3 ml of dimethylformamide are stirred at room temperature for 3 hours. After the mixture has been concentrated, petroleum ether is added, the mixture is filtered and the filtrate is concentrated again.

Bulb tube distillation of the residue at 150° C. (0.5 mbar) gives 3.28 g (89.6% of theory) of N-(2,4,6-trichlorophenyl)-trifluoroacetohydrazide chloride of refractive index $n_D^{20}$ 1.549.

The following N-arylhydrazide halides of the general formula (II) are obtained in a corresponding manner and in accordance with the general statements on the preparation:

| Ex. No. | R¹ | Hal | Ar | Physical constants |
|---|---|---|---|---|
| II-3 | $CF_3$ | Br | 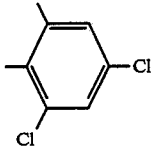 2,5-dichlorophenyl | bp 125° C./ 0,08 mbar |
| II-4 | $CF_3$ | Cl | 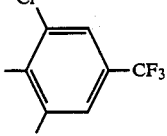 2,6-dichloro-4-CF₃-phenyl | bp 130° C./ 0,5 mbar |
| II-5 | $CF_3$ | Br | 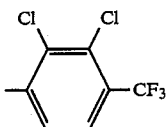 2,3-dichloro-4-CF₃-phenyl | mp 62–63° C. |
| II-6 | $CF_3$ | Br | 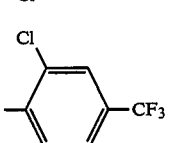 2-chloro-4-CF₃-phenyl | bp 95° C./ 0.05 mbar |
| II-7 | $CF_3$ | Cl | 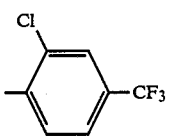 2-chloro-4-CF₃-phenyl | bp 90° C./ 0,13 mbar |
| II-8 | $CF_3$ | Br | 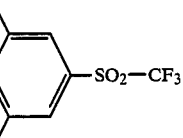 2,6-dichloro-4-SO₂CF₃-phenyl | mp 48–50° C. |

Example X-1

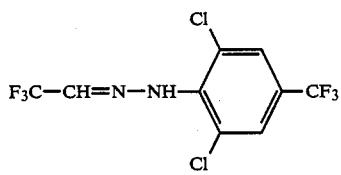

A mixture of 100 g (0.69 mol) of trifluoroacetaldehyde ethyl hemi-acetal and 169.1 g (0.69 mol) of 2,6-dichloro-4-trifluoromethylphenylhydrazine is heated at 100° C. for 6 hours. After the volatile components have been removed, the residue is recrystallized from petroleum ether.

200 g (89% of theory) of trifluoroacetaldehyde N-(2,6-dichloro-4-trifluoromethylphenyl)-hydrazone of melting point 45° C. to 46° C. are isolated.

The following aldehyde N-arylhydrazones of the general and in accordance with the general statements on the preparation:

$$R^1-CH=NH-Ar \qquad (X)$$

| Ex. No. | R¹ | Ar | Melting Point /° C. |
|---|---|---|---|
| X-2 | $CF_3$ | 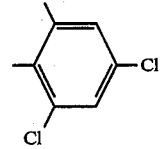 | 43–45 |
| X-3 | $CF_3$ | 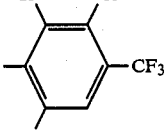 | 50–52 |
| X-4 | $CF_3$ |  | 63–65 |
| X-5 | $CF_3$ | 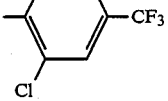 | 124–126 |

USE EXAMPLES

The compound shown below was employed as a comparison substance in the use examples which follow:

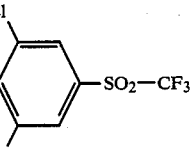

4-cyano-5-propionamido-1-(2,4,6-trichlorophenyl)-pyrazole (known from DE-OS (German Published Specification) 3,226,513)

Example A

Phaedon Larvae test
Solvent: 7 parts by weight of dimethylformamide Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the following compounds from the prepration examples show a superior activity compared with the prior art: 3, 7, 13, 15, 17, 18, 19 and 20.

Example B

Seed treatment test/root-systemic action
Test insect: *Phaedon cochleariae* beetles
Test plant: *Brassica oleracea*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The cabbage seed is treated with this active compound preparation at the application rates required. The cabbage is sown in 0.5 liter pots containing standarized soils at a room temperature of 20° C.

The active compound can thus be taken up from the soil by the plant roots and transported into the leaves.

For detection of the root-systemic effect, the leaves only are infested with the abovementioned test insects after 14 days. After a further 3 days, the evaluation is carried out by counting or estimating the dead insects. The root-systemic action of the active compound is derived from the mortality figures. It is 100% if all the test insects have been killed and 0% if just as many test insects are still alive as in the untreated control.

In this test, for example, the following compound of the preparation examples shows a superior action compared with the prior art: 3.

Example C

Seed treatment test/soil insects
Test insect: *Phorbia antiqua* grubs in the soil
Test plant: *Allium cepa*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The onion seed is treated with this active compound preparation at the application rates required. They are sown in 0.5 liter pots containing standardized soils at a greenhouse temperature of 20° C.

After emergence of the onions, they are infected artificially with onion fly eggs.

Evaluation is carried out after 14 days. The degree of action is 100% if all the onion plants remain standing, and 0% if all the test plants have been destroyed (as in the untreated control).

In this test, for example, the following compound of the preparation examples shows a superior action compared with the prior art: 3.

Example D $LT_{100}$ test for Diptera

Test insects: *Musca domestica* (resistant)
Solvent: acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per $m^2$ of filter paper varies, depending on the concentration of the active compound solution. The stated number of test insects is then introduced into the Petri dish, and the dish is covered with a glass lid.

The condition of the test insectsis checked continuously. The time required for a 100% knock-down effect is determined.

In this test, for example, the following compounds from the preparation examples show a superior action compared with the prior art: 1, 3 and 13.

Example E

Test insects: *Blattella germanica*
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per $m^2$ of filter paper varies, depending on the concentration of the active compound solution. About 20 of the test insects are then introduce into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, for example, the following compounds from the preparation examples show a superior action compared with the prior art: 1, 3 and 13.

It will be appreciated that the instant specification and claims are set forth by way of illustration and not limitation, and that various modifications and changes may be made without departing from the spirit and scope of the present invention.

We claim:

1. A 3-halogenoalkyl-1-aryl-pyrazole of the formula

in which
$R^1$ represents halogenoalkyl,
$R^2$ represents hydroxycarbonyl, alkoxycarbonyl, alkenyloxycarbonyl or alkinyloxycarbonyl,
$R^3$ represents hydrogen, alkyl, halogenoalkyl or cycloalkyl and Ar represents substituted phenyl, with the exception of the 2,4-dinitrophenyl radical.

2. A 3-halogenoalkyl-1-aryl-pyrazole according to claim 1,
in which
$R^1$ represents straight-chain or branched hologenoalkyl with 1 to 4 carbon atoms and 1 to 9 identical or different halogen atoms,
$R^2$ represents hydroxycarbonyl, straight-chain or branched alkoxycarbonyl, straight-chain or branched alkenyloxycarbonyl or straight-chain or branched alkinyloxycarbonyl,
$R^3$ represents hydrogen, or represents in each case straight-chain or branched alkyl or halogenoalkyl with in each case 1 to 4 carbon atoms and, in the case of the halogenoalkyl, with 1 to 9 identical or different halogen atoms, or represents cycloalkyl with 3 to 7 carbon atoms and
Ar represents phenyl which is substituted by one or more substituents, with the exception of the 2,4-dinitrophenyl radical, the substituents being independently selected from the group consisting of halogen, cyano, nitro and in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl or alkoxycarbonyl with in each case 1 to 4 carbon atoms in the individual alkyl parts and, where appropriate, 1 to 9 identical or different halogen atoms.

3. A 3-halogenoalkyl-1-aryl-pyrazole according to claim 1,
in which
$R^1$ represents trifluoromethyl, dichlorofluoromethyl, difluorochloromethyl, difluoromethyl, trifluoroethyl, trifluorochloroethyl, trifluorodichloroethyl, difluorodichloroethyl, tetrafluoroethyl, pentafluoroethyl, heptafluoropropyl or nonafluorobutyl,
$R^2$ represents hydroxycarbonyl, methoxycarbonyl or ethoxycarbonyl,
$R^3$ represents hydrogen, methyl, ethyl, n- or i-propyl, n-, i-, s- or t-butyl, trifluoromethyl, dichlorofluoromethyl, difluorochloromethyl, difluoromethyl, trifluoroethyl, tetrafluoroethyl, pentafluoroethyl, trifluorochloroethyl, trifluorodichloroethyl, difluorodichloroethyl, heptafluoropropyl or nonafluorobutyl, or represents cyclopropyl, cyclobutyl, cyclopentyl or cyclohexyl and
Ar represents phenyl which is substituted by one to five substituents, with the exception of the 2,4-dinitrophenyl radical the substituents being independently selected from the group consisting of fluorine, chlorine, bromine, iodine, cyano, nitro, methyl, ethyl, n-or i-propyl, n-, i-, s- or t-butyl, methoxy, ethoxy, methylthio, methylsulphinyl, methylsulphonyl, methoxycarbonyl, ethoxycarbonyl, trifluoromethyl, dichlorofluoromethyl, difluorochloromethyl, difluoromethyl, pentafluoroethyl, tetrafluoroethyl, trifluorochloroethyl, trifluoroethyl, difluorochloroethyl, trifluorodichloroethyl or a radical —X—$R^4$,
wherein
X represents oxygen, sulphur, sulphinyl or sulphonyl and
$R^4$ represents trifluoromethyl, dichlorofluoromethyl, difluorochloromethyl, difluoromethyl, pentafluoroethyl, tetrafluoroethyl, trifluorochloroethyl, trifluoroethyl, difluorochloroethyl or trifluorodichloroethyl.

4. A compound according to claim 1, wherein such compound is 4-methoxycarbonyl-3-trifluoromethyl-1-(2,6-dichloro-4-trifluoromethylphenyl)-pyrazole of the formula

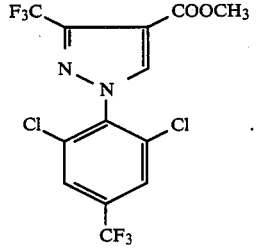

5. An arthropodicidal composition comprising an arthropodicidally effective amount of a compound according to claim 1 and a diluent.

6. A method of combating arthropods which comprises applying to such arthropods or to an arthropod habitat an arthropodicidally effective amount of a compound according to claim 1.

7. The method according to claim 6, wherein such compound is
4-methoxycarbonyl-3-trifluoromethyl-1-(2,6-dichloro-4-trifluoromethylphenyl)-pyrazole.

* * * * *